United States Patent [19]

Collier

[11] Patent Number: 4,731,088
[45] Date of Patent: Mar. 15, 1988

[54] ENCLOSURE MEMBER FOR PROSTHETIC JOINT

[75] Inventor: John P. Collier, Hanover, N.H.

[73] Assignee: Boehringer Mannheim Corp, Indianapolis, Ind.

[21] Appl. No.: 869,592

[22] Filed: Jun. 2, 1986

[51] Int. Cl.[4] .............................................. A61F 2/34
[52] U.S. Cl. ...................................... 623/22; 623/18
[58] Field of Search ...................... 623/16–23

[56] References Cited

U.S. PATENT DOCUMENTS

| | | | |
|---|---|---|---|
| 3,593,342 | 7/1971 | Niebauer et al. | 623/18 |
| 3,605,123 | 9/1971 | Hahn | 623/16 |
| 3,656,184 | 4/1972 | Chambers | 623/18 |
| 3,739,403 | 6/1973 | Nicolle | 623/21 |
| 3,745,590 | 7/1973 | Stubstad | 623/18 |
| 3,808,606 | 5/1974 | Tronzo | 623/16 |
| 3,818,513 | 6/1974 | Pillet | 623/18 |
| 3,864,758 | 2/1975 | Yakich | 623/23 |
| 3,869,730 | 3/1975 | Skobel | 623/19 |
| 3,879,767 | 4/1975 | Stubstad | 623/18 |
| 3,886,600 | 6/1975 | Kahn et al. | 623/18 |
| 3,938,198 | 2/1976 | Kahn et al. | 623/18 |
| 3,986,212 | 10/1976 | Sauer | 623/18 |
| 4,038,703 | 8/1977 | Bokros | 623/18 |
| 4,086,665 | 5/1978 | Poirier | 623/1 |
| 4,205,399 | 6/1980 | Shalaby et al. | 623/1 |
| 4,208,745 | 6/1980 | Okita | 623/1 |
| 4,340,091 | 7/1982 | Skelton et al. | 623/1 |

OTHER PUBLICATIONS

Goldring, S. R. et al., "The Synovial-Like Membrane at the Bone-Cement Interface in Loose Total Hip Rep. & Its Proposed Role in Bone Lysis", J. Bone and Joint Surgery, 65-A: 575–583, Jun. 1983.

Primary Examiner—Richard J. Apley
Assistant Examiner—David J. Isabella
Attorney, Agent, or Firm—Perman & Green

[57] ABSTRACT

A flexible enclosure is applied to a prosthetic joint to isolate wear particles which are produced by interengagement between the components of the joint. The enclosure overlies the joint, and is affixed to the respective joint components proximate to its ends. The enclosure may be impermeable to fluids and contain a synthetic synovial fluid for lubrication of the joint. Alternatively, the enclosure may be porous having pores of a size ranging between 0.1 and 100 microns across so as to maintain larger wear particles which the body cannot assimilate.

8 Claims, 6 Drawing Figures

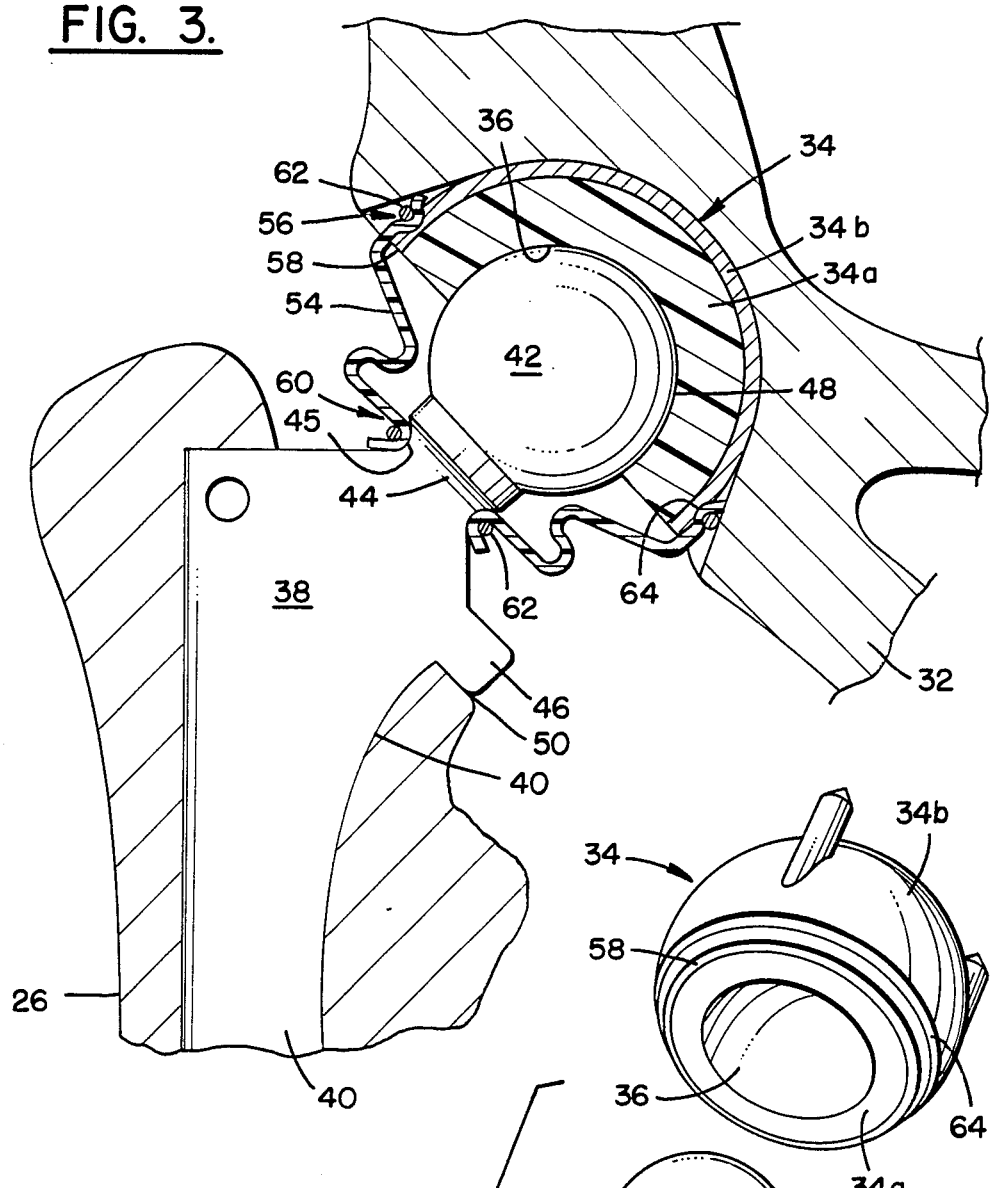

ENCLOSURE MEMBER FOR PROSTHETIC JOINT

BACKGROUND OF THE INVENTION

I. Field of the Invention

The present invention relates generally to the field of orthopedic surgery and has particular application to a total artificial joint and the implantation thereof.

II. Description of the Prior Art

This invention relates broadly to means for transferring forces imposed on load bearing portions of artificial joints to bone in humans and animals. While the present invention is applicable for use with implants of various types and in numerous applications in human and animal joints, it will be described herein, for purposes of example only, as being specifically adapted for use in transferring the load on the femoral head replacement of a total hip joint prosthesis, such as the Charnley type, to the femur. Although hip prostheses will be used for illustrative purposes only, features of the invention will be stated in a generic form so that they are applicable to all joint prostheses and to the geometric and biomedical properties of all animal and human joints.

The artificial hip joint is intended as a replacement for both parts of the human hip joint. The natural hip joint consists of a ball-like member at the head of the femur or thighbone, this member being rotatable in a socket, termed the acetabulum, in the pelvis. When this joint becomes damaged or diseased, it is the practice to replace the femoral head with a prosthesis including a ball member attached to the femur by a neck and stem which fits into the medullary canal, and to fit a corresponding artificial socket member into the acetabulum, which may be suitably enlarged for the purpose.

Most of the currently available total joint replacements are comprised of a metal component articulating against a plastic component. For example, the spherical articulating, or bearing, surfaces of the typical prosthetic hip joint include an implanted femoral component having a spherical surface of cobalt/chromium alloy articulating against an acetabular component, or cup, made of high-density polyethylene.

In the late 1960's, Sir John Charnley experimented with the use of tetrafluoroethylene, commonly known by the trademark TEFLON, for the surface of the acetabular component, working against the usual metal component, but the results were less than satisfactory. While TEFLON material in its bulk form is inert in the body, the TEFLON wear debris generated by the articulating surfaces rubbing against one another caused severe histiocytic reactions in the surrounding tissue with resulting trauma and pain experienced by the patient. The reaction was such that the TEFLON components eventually required removal.

More recent hip prostheses have utilized acetabular sockets of high density polyethylene, and it has been the practice to utilize a bone cement, polymethyl methacrylate, for example, to retain the implanted component. There is some uncertainty as to which of the two polymeric materials has been the major source of wear particles that have caused observed adverse tissue reactions, although it has generally been assumed to be the bone cement.

As the technology has progressed, porous coatings have begun to replace bone cement in a high proportion of implantations. This permits natural bone ingrowth, eliminating the need for bone cement and avoiding problems caused by the cementitious wear particles. This new technology has not been in use long enough to determine the extent of problems resulting from wear particles resulting from the interaction between the metal component and the plastic component. However, as prostheses remain in use for longer periods and are used for younger and more active patients, it is inevitable that wear particles from the polyethylene articulating surfaces will become a problem. Hence some means of isolating these particles from the surrounding cellular tissue would be highly beneficial.

For example, there is a substantial and growing body of evidence to the effect that wear particles lead to prosthetic loosening and eventually to catastrophic failure of the prosthesis. In a paper published in the American Volume of *The Journal of Bone and Joint Surgery*, Vol. 65-A, No. 5 (June 1983) on page 575, Goldring et al state:

"CLINICAL RELEVANCE: This transformation of tissue at the bone-cement interface in patients with a non-septic, loose total hip component to a synovial-like tissue with the capacity to generate 10 prostaglandin $E_2$ and collagenase may explain the progressive lysis of bone that is seen in some patients with loose cemented total joint implants. Loosening of the component may be a stimulus to the synthetic activity of this tissue, which leads 15 to further resorption of bone. Understanding and the possibility of pharmacological control of this membrane may contribute to improved duration of total joint implants."

It was with knowledge of the current state of the art and in view of the problems previously encountered as noted above, that the present invention was conceived and has now been reduced to practice.

SUMMARY OF THE INVENTION

The present invention pertains to implanted total prosthetic joints such as hips and knees and a primary object of the invention is to isolate the joint from its surrounding tissue by enclosing it within a flexible member, thereby preventing wear particles from causing histiocytic reactions in the surrounding tissue. It is proposed to provide, as a permanent part of the prosthetic joint an enclosure of flexible, biologically compatible material which is attached to each component of a prosthetic joint and which isolates the joint from its surrounding tissue. For example in the hip prosthesis, one end of the enclosure would be attached to the femoral component and the other end to the acetabular component, the enclosure material being flexible enough so that it does not impair maximum normal joint motion. Examples of such suitable biocompatible materials include silicone rubber and woven polymers such as those commonly sold under the trademarks GORTEX and DACRON which are used in prosthetic venous grafts.

The enclosure would not only avoid adverse tissue reactions by preventing wear particles from entering the surrounding tissue but in one embodiment, it would also permit the use within the enclosure of a lubricating fluid with properties optimized for the articulating materials used, rather than depending on the less than ideal properties of body fluid present after the natural synovial fluid has been removed during the joint implantation surgery. In this instance, it would be impervious to fluid. Silicone rubber would be an excellent choice of material for this application. This would greatly reduce the production of wear particles and increase the life of the joint. In another embodiment, using GORTEX or an equivalent porous material or fabric or a semi-permeable membrane, it would permit the passage of body fluids therethrough while preventing wear particles greater than a predetermined size to escape to the rest of the body. Being transparent to X-ray in either event, the enclosure would not interfere in any way with routine examinations of the joint.

Other and further features, objects, advantages, and benefits of the invention will become apparent from the following description taken in conjunction with the following drawings. It is to be understood that both the foregoing general description and the following detailed description are exemplary and explanatory but not restrictive of the invention. The accompanying drawings which are incorporated in and constitute a part of this invention, illustrate some of the embodiments of the invention and, together with the description, serve to explain the principles of the invention in general terms. Like numerals refer to like parts throughout the disclosure.

BRIEF DESCRIPTION OF THE DRAWINGS

FIG. 3 is an enlarged detail elevation view of parts illustrated in FIG. 2 with additional portions being cut away and in section;

FIG. 4 is a detail perspective exploded view of parts illustrated in FIGS. 2 and 3;

DETAILED DESCRIPTION OF THE PREFERRED EMBODIMENT

Turn now to the drawings which illustrate the invention as applied to a reconstructed hip joint which may be that of an animal or of a human being. The hip joint is chosen for illustration for simplicity's sake since it is probably the easiest joint to visualize. It will be understood, however, that the invention can be utilized at any major joint of the body whether it be hip, knee, elbow, shoulder, wrist, or the like.

Figure 1:
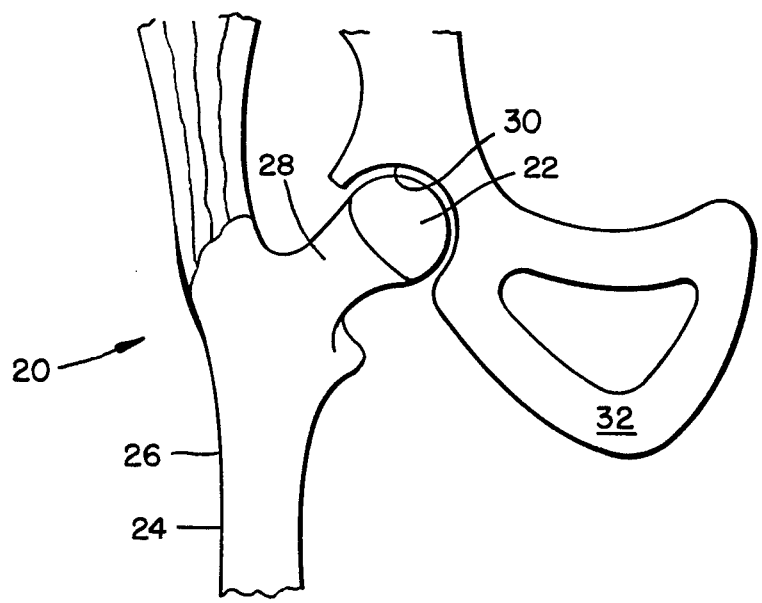
FIG. 1 is a detail elevation view diagrammatically illustrating a natural hip joint.
Figure 2:
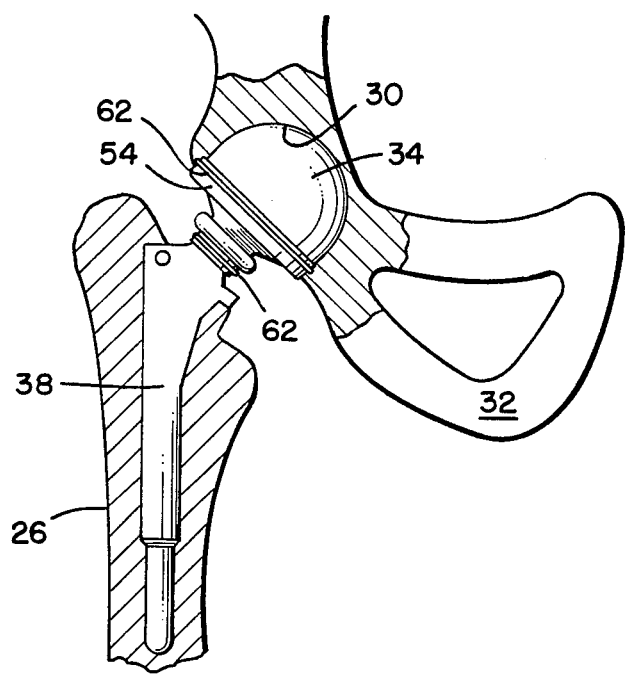
FIG. 2 is a partly sectioned elevation view diagrammatically illustrating a total hip replacement incorporating the invention.

A natural hip joint 20, as illustrated in FIG. 1, is a ball-in-socket joint wherein the head 22 is connected to the shaft 24 of the femur 26 by means of a neck 28. The head 22 is generally of hemispherical shape and rotatably engaged with the acetabulum 30 of the pelvis 32. When the hip joint 20 becomes damaged or diseased, it may become desirable to replace elements of the structure just described. Such an artificial structure is illustrated in FIGS. 2-4 and its emplacement is performed by means of a surgical procedure. Specifically, with the patient under anesthetic, and with the hip joint exposed, the femoral head 22 is separated from the acetabulum 30. A reamer or similar bone cutting tool is utilized to reshape the acetabulum to complimentarily receive an acetabular component 34 which has a spherical inner surface 36. The acetabular component 34 is suitably attached to the pelvis 32 so that it does not rotate or otherwise move relative to the hip bone.

As to the femur 26, the head 22 and at least a portion of the neck 28 are surgically removed from the shaft 24. Thereupon, a complimentary part of the prosthesis, namely a femoral component 38, is secured to the femur 26. Specifically, the femoral component 38 includes a shank 40, a ball 42, a neck 44 intermediate the ball and the shank, and often a collar 46 carried at an expanded end of the shank 40. The ball 42 has a spherical surface 48. The femoral component 38 is then inserted into the femur 26 with the shank 40 of the component 38 being driven downwardly through the approximate center of the shaft 24 of the femur 26 until the collar 46 is brought into contact with a resected medial neck 50 of the femur. The ball 42 is designed to have a slightly smaller radius than that of the inner surface 36 of the acetabular component 34. The spherical surface 48 and the inner surface 36 are polished such that when the ball 42 is received within the acetabular component 34 as illustrated in FIGS. 2 and 3, the ball is free to rotate relative to the acetabular component with a minimum of friction. Typically at the present time, the acetabular component 34 is composed of a bearing portion 34a composed of an inert plastic material such as high density polyethylene, and an outer cup-shaped support member 34b composed of a suitable metal such as a cobalt alloy or a titanium alloy. The femoral component 38 is formed of a hard, biologically acceptable metal, such as a cobalt-chromium-molybdenum alloy or a titanium alloy.

As seen in FIGS. 2 and 3, the invention comprises a sheath 54 of a flexible, biologically inert material having a thickness generally in the range of 20 microns to one millimeter. The sheath is generally tubular in shape, one end 56 being affixed and sealed to a terminal lip 58 of the acetabular component 34. An opposite end 60 of the sheath 54 is affixed and sealed to the outer surface of the femoral component 38 adjacent the neck 44 or the collar 40. The ends of the sheath 54 may be sealingly affixed or engaged by means of a suitable adhesive, or by mechanical or frictional bonding as in the event the sheath is composed of a heat shrinkable material, or in any other suitable fashion. One such other suitable method is illustrated in FIGS. 2 and 3 according to which suitable elongate material 62 such as suture or wire encircles the sheath 54 proximate to its ends. Proximate to the end 60, the elongate material encircles the sheath in the region of the neck 44 where it secures the sheath to a groove 45. Proximate to the end 56, the elongate material encircles the sheath, preferably with the aid of an annular groove 64 formed near the base of the acetabular component 34.

The sheath may be porous or non-porous, depending upon whether it is desired to have body fluids able to move in and out of the joint. If it is porous, it may be fabricated of a material such as GORTEX or woven DACRON having pores which are sufficiently small that wear debris cannot pass out of the articulating joint and into the host tissue where it could cause an inflammatory response and lead to prosthetic loosening. In this instance, the size of the pores could be in the range of 0.1 to 100 microns, but would preferably be in the range of 1 to 10 microns. The rationale for this is that the lymph system of the body can properly dispose of small amounts of very small wear particles. Above this size range, the particles can cause problems having the nature of causing inflamation and possibly loosening of the prosthetic appliance.

It was also noted that the sheath 54 could be non-permeable and, in that instance, a suitable material for its composition would be silicone rubber. In that instance, it would be desirable to fill the joint space enclosed by the sheath with a suitable liquid, such as a sterile saline solution or other replacement of the synovial fluid, and thereby potentially improve the lubrication of the joint while at the same time maintaining the wear debris from the joint within the synovial sheath 54.

It is intended that the sheath 54 in no way constrain the motion between the articulating surfaces as represented by the acetabular component 34 and the femoral component 38.

It is also envisioned as quite possible in either instance, after considerable wear has occurred, that the wear particles could be aspirated from the joint using conventional techniques. One typical technique requires concentric hollow tubes, one of which provides fresh saline solution or its equivalent, to the joint, and the other provides an exit for the wear debris. Additionally, in the event the polyethylene insert becomes worn out, the sheath 54 can be temporarily disconnected, the old polyethylene insert replaced with a new one, the wear particles removed, and the sheath re-attached.

Figure 5:
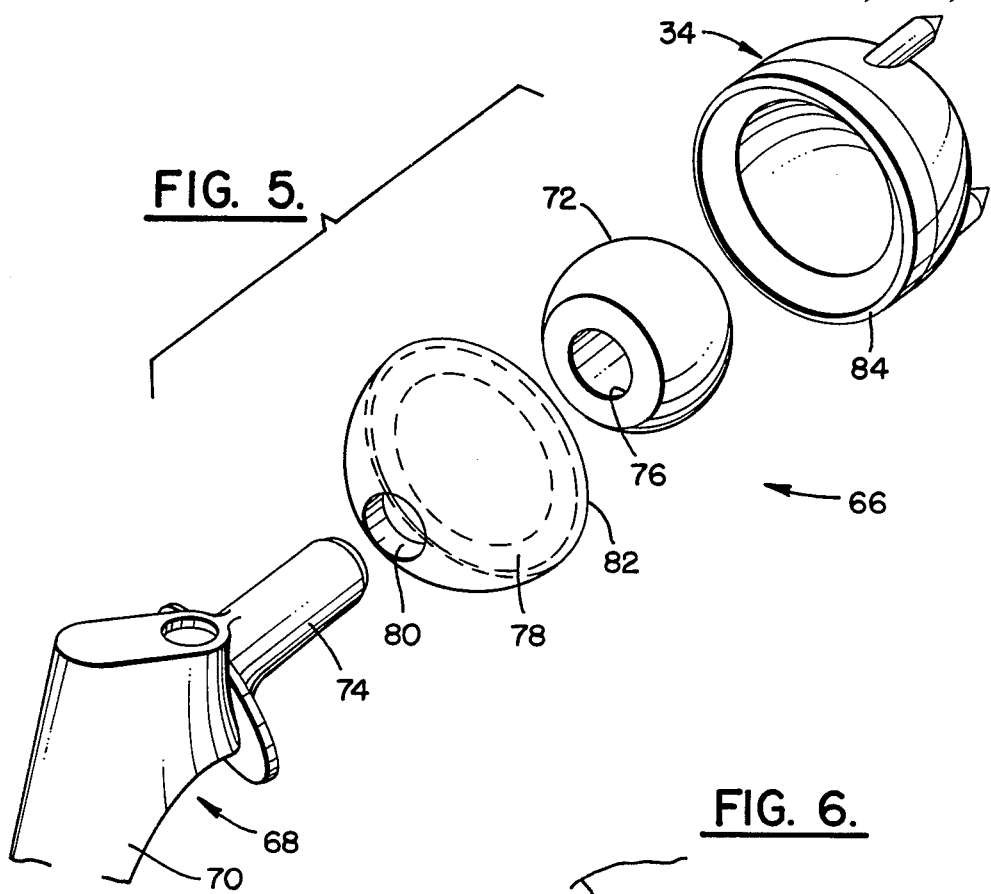
FIG. 5 is a perspective exploded view illustrating another embodiment of the invention.
Figure 6:
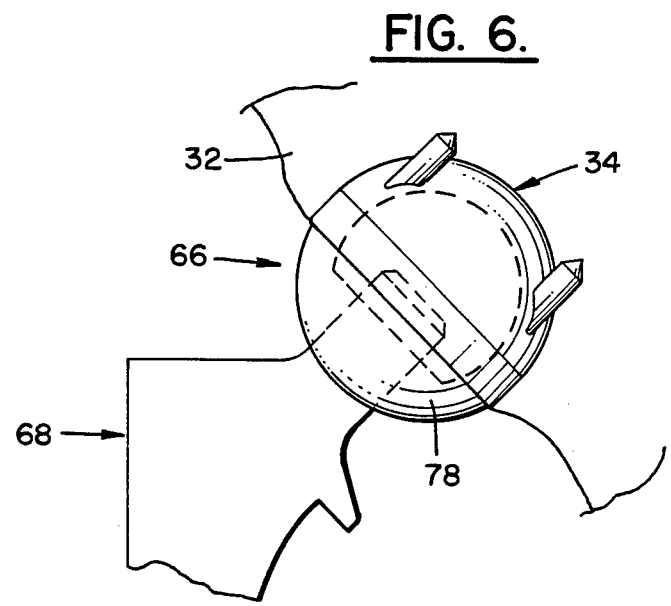
FIG. 6 is a side elevation view of the parts illustrated in FIG. 5 but in their assembled condition.

Another embodiment of the invention is presented in FIGS. 5 and 6 which illustrate a flexible enclosure construction 66 which, by way of example, is utilized in conjunction with a hip prosthesis. In this instance, the acetabular component 34 may be substantially the same as that previously described. However, the femoral component 68 is somewhat modified. As previously, the femoral component includes a shank 70 and a modular head system comprising a ball 72 and a neck 74 formed, for example, with a so-called Morse taper according to a commonly used arrangement. The ball 72 is hollowed-out as at 76 and is mounted on the neck 74 by way of a force fit.

In this instance, prior to mounting of the ball 72 on the neck 74, a flexible, generally ring like enclosure member 78 is mounted onto the neck 74. In order to accomplish this construction, the enclosure member 78 is provided with an axial bore 80 which extends entirely through the member and is of a size to assure a tight fit with the neck 74. The enclosure member 78 may be composed of the same materials mentioned previously with respect to the sheath 54. The enclosure member 78 is also formed with a continuous peripheral edge 82 which is generally sized and shaped in a complementary fashion with respect to a rim 84 on the acetabular component 34. Thus, when the prosthesis, as modified by this embodiment of the invention, assumes its completed form as illustrated in FIG. 6, the peripheral edge 82 matingly engages the rim 84 of the acetabular component 34. This mating engagement is intended to be a sealing engagement. That is, with the construction illustrated in FIG. 6, the support member 34b (as illustrated in FIG. 3) and the enclosure member 78, acting together, serve to isolate the inter-engaging region of the acetabular component and of the femoral component from the remainder of the body.

It will be appreciated that the enclosure member 78 must be sufficiently flexible to permit the full range of normal motion between the acetabular component and the femoral component as in the embodiment using the sheath 54. Also, the sealing engagement between the enclosure member and the acetabular component may be of any suitable nature including, but not necessarily limited to, bonding by use of adhesives, or otherwise, mounting by way of a friction fit, or by a mechanical connection as by the use of suture or wire.

The invention, then, recognizes substantial evidence to the effect that the plastic wear particles within the tissue of humans causes the formation of prostaglandins which have been associated with the fibrous membranes surrounding loosened prostheses of all types. Furthermore, it is believed that the wear debris causes, at least in part, the loosening of prostheses. It is recognized as being very difficult to reduce the wear generated by metal on plastic articulating surfaces. Nevertheless, it should be possible to keep the wear particles generated by such articulation away from the host tissue. Indeed, that is what has been described herein, namely, a barrier between the articulating surfaces and the host to keep all wear debris contained and away from the host tissue.

While the preferred embodiments of the invention have been disclosed in detail, it should be understood by those skilled in the art that various modifications may be made to the illustrated embodiments without departing from the scope as described in the specification and defined in the appended claims.

What is claimed is:

1. In an artificial joint for replacing a damaged natural joint in a skeletal structure of a body including a prosthesis having a first cooperating member secured to a first bone and a second cooperating member secured to a second bone, said first and second cooperating members being interengaging and relatively movable to permit relative movement between the first and second bones, the improvement comprising:
   a generally tubular flexible porous sheath having pores of a size less than 10 microns across surrounding the interengaging region between said first and second members and having first and second opposed ends, said first end being affixed to said first member, said second end being affixed to said second member, said sheath being capable of permitting the passage of fluid therethrough while isolating from the remainder of the body wear particles which develop at the interengaging region of said first member and said second member.

2. The improvement in artificial joints as set forth in claim 1
   wherein said first member includes a cup-shaped socket composed of a plastic material and wherein said second member includes a ball member composed of metal.

3. The improvement in artificial joints as set forth in claim 1
   wherein said sheath has a thickness generally in the range of 20 microns to 1 mm.

4. The improvement in artificial joints as set forth in claim 1
   wherein said sheath is composed of a woven polymer material.

5. An artificial joint for replacing a damaged natural joint in a skeletal structure of a body comprising:
   a cup-shaped socket member fittingly received in a recess of a first bone and having a continuous rim adjacent the outer surface of the first bone;
   an interengaging region including a prosthesis including:
   a ball member rotatable in said socket member;
   an elongated shank for securing said ball member to a second bone separate from the first bone;
   a neck member of reduced size interconnecting said ball member and said shank; and
   a generally tubular flexible porous enclosure means having pores of a size less than 10 microns; and said enclosure means being sealingly engaged with and extending between said first and second members for isolating the interengaging region of said ball member and said socket member from the remainder of the body.

6. The improvement in artificial joints as set forth in claim 5 wherein said flexible enclosure means includes:
a generally tubular flexible sheath having opposed ends, one of said ends being fixed and sealed to said rim, the other of said ends being fixed and sealed to said neck member.

7. The improvement in artificial joints as set forth in claim 5 wherein said flexible enclosure means includes:
a ring-shaped member having an axial bore therethrough fittingly received on said neck member and having a peripheral edge which matingly engages said rim of said socket member;

whereby said socket member and said ring-shaped member sealingly envelops said ball member therein.

8. An artificial joint for replacing a damaged natural joint in a skeletal structure of a body including a prosthesis having a first cooperating member secured to a first bone and a second cooperating member secured to a second bone, the first and second cooperating members being interengaging and relatively movable to permit relative movement between the first and second bones, the improvement comprising:
a generally tubular flexible porous sheath having pores of a size less than 10 microns across surrounding the interengaging region between said first and second members and having first and second opposed ends, said first end being affixed to said first member, said second end being affixed to said second member, said sheath being capable of permitting the passage of fluid therethrough while isolating from the remainder of the body wear particles which develop at the interengaging region of the first member and the second member.

* * * * *